United States Patent
Bunch et al.

(10) Patent No.: US 9,314,578 B2
(45) Date of Patent: *Apr. 19, 2016

(54) DEVICE FOR DISPENSING A PLURALITY OF UNITARY DOSES OF DRY POWDER, AND INHALER COMPRISING SUCH DEVICE

(71) Applicants: Pfizer Limited, Kent (GB); Petra Jane Harris

(72) Inventors: Louise Annabel Bunch, Cambridgeshire (GB); Paul George Harris, Cambridgeshire (GB)

(73) Assignee: PFIZER LTD., Kent (GB)

(*) Notice: Subject to any disclaimer, the term of this patent is extended or adjusted under 35 U.S.C. 154(b) by 397 days.

This patent is subject to a terminal disclaimer.

(21) Appl. No.: 13/951,668

(22) Filed: Jul. 26, 2013

(65) Prior Publication Data

US 2013/0306071 A1    Nov. 21, 2013

Related U.S. Application Data

(63) Continuation of application No. 13/010,195, filed on Jan. 20, 2011, now Pat. No. 8,528,549.

(60) Provisional application No. 61/296,629, filed on Jan. 20, 2010.

(51) Int. Cl.
*A61M 15/00* (2006.01)

(52) U.S. Cl.
CPC ........ *A61M 15/0028* (2013.01); *A61M 15/0026* (2014.02); *A61M 15/0045* (2013.01);
(Continued)

(58) Field of Classification Search
CPC ..... A61J 7/0481; A61J 7/049; A61M 11/003; A61M 15/00; A61M 15/0003; A61M 15/0006; A61M 15/0008; A61M 15/0021; A61M 15/0025; A61M 15/0026; A61M 15/0028; A61M 15/0031; A61M 15/0033; A61M 15/0035; A61M 15/0036; A61M 15/0041; A61M 15/0043; A61M 15/0045; A61M 15/0048; A61M 15/0051; A61M 15/0055; A61M 15/0058; A61M 15/0061; A61M 15/0068; A61M 15/007; A61M 15/0073; A61M 15/0075; A61M 15/008; A61M 15/0091; A61M 15/08; A61M 16/10; A61M 16/127; A61M 2016/0024; A61M 2202/064; A61M 2205/073; A61M 2205/12; A61M 2205/581; A61M 2205/8206; A61M 2206/16; B23P 11/00; B65B 1/04; B65D 83/0445; B65D 83/06; G06M 1/248; G08B 1/00; Y10T 29/49826
USPC ............. 128/200.11–200.24, 200.14, 200.23, 128/203.12, 203.15, 203.19, 203.21, 128/205.23; 222/129–145.8, 144, 153.02, 222/153.04, 23
See application file for complete search history.

(56) References Cited

U.S. PATENT DOCUMENTS 7,219,665 B1 *  5/2007  Braithwaite ...... A61M 15/0045
                                                    128/203.12
(Continued)

FOREIGN PATENT DOCUMENTS

WO    2005002654    1/2005

OTHER PUBLICATIONS

"International Search Report issued for PCT/IB2011/05029 dated May 18, 2011".
(Continued)

Primary Examiner — Annette Dixon
(74) Attorney, Agent, or Firm — Kramer & Amado P.C.

(57) ABSTRACT

Various embodiments relate to a device for dispensing a plurality of unitary doses of dry powder. The device includes: a casing; first and second supports respectively for two carriers each having a plurality of housings for respective unitary doses adapted to be connected to the mouthpiece for inhalation of the dose, the first and second supports being moveably mounted within the casing for sequentially connecting the housings to the mouthpiece; an indexing mechanism adapted to engage and move the first and second supports; and a changeover mechanism adapted to cause the device to pass from a first dispensing state to a second dispensing state and lock the second support in its stationary position while the device is in the first dispensing state, and to lock the first support in its stationary position while the device is in the second dispensing state.

19 Claims, 10 Drawing Sheets

(52) U.S. Cl.
CPC ....... *A61M15/0048* (2014.02); *A61M 15/0061* (2014.02); *A61M 15/0075* (2014.02); *A61M 2202/064* (2013.01)

(56) References Cited

U.S. PATENT DOCUMENTS

| | | | | |
|---|---|---|---|---|
| 7,571,723 B2* | 8/2009 | Braithwaite | ...... | A61M 15/0045 128/203.12 |
| 7,571,724 B2* | 8/2009 | Braithwaite | ...... | A61M 15/0045 128/203.15 |
| 8,181,645 B2* | 5/2012 | Houzego | ...... | A61M 15/0045 128/203.12 |
| 8,205,614 B2* | 6/2012 | Braithwaite | ...... | A61M 15/0045 128/200.24 |
| 2005/0268909 A1 | 12/2005 | Bonney et al. | | |
| 2007/0163580 A1* | 7/2007 | Braithwaite | ...... | A61M 15/0045 128/203.21 |
| 2008/0295834 A1 | 12/2008 | Thoemmes et al. | | |
| 2009/0293874 A1 | 12/2009 | Braithwaite | | |

OTHER PUBLICATIONS

"PCT Written Opinion for PCT/IB2011/050209 dated May 18, 2011".

* cited by examiner

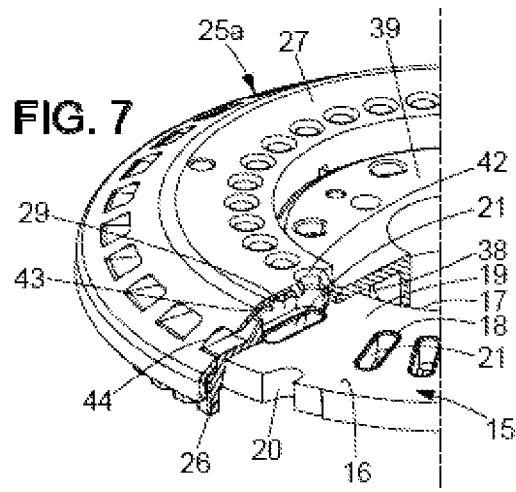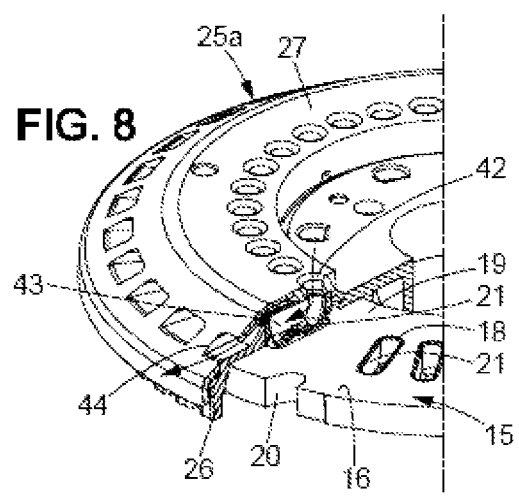

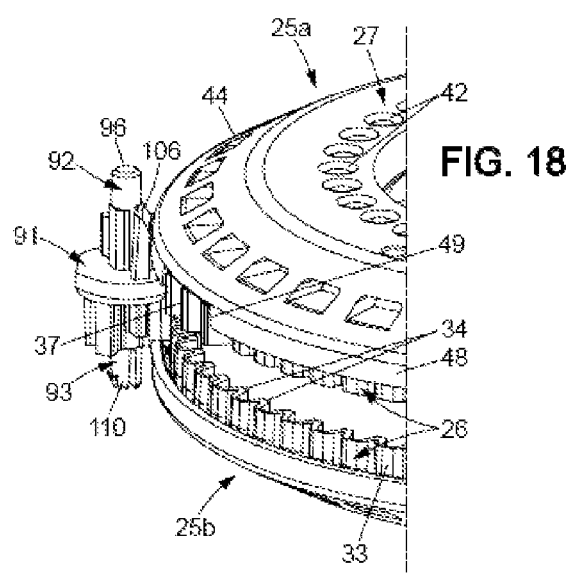

DEVICE FOR DISPENSING A PLURALITY OF UNITARY DOSES OF DRY POWDER, AND INHALER COMPRISING SUCH DEVICE

This application is a continuation application of U.S. application Ser. No. 13/010,195 filed on Jan. 20, 2011.

This application claims the benefit under 35 U.S.C. §119 (e) of U.S. Provisional Patent Application No. 61/296,629, filed on Jan. 20, 2010, the disclosure of which is hereby incorporated by reference in its entirety.

TECHNICAL FIELD

The invention relates to a device for dispensing a plurality of unitary doses of dry powder, and to an inhaler comprising such device.

BACKGROUND

In particular, the invention relates to a device for dispensing a plurality of unitary doses of dry powder, comprising:

a casing provided with a mouthpiece for inhalation by a user, first and second supports respectively for two carriers each having a plurality of housings for respective unitary doses adapted to be connected to the mouthpiece for inhalation of the dose, the first and second supports being moveably mounted within the casing for sequentially connecting the housings to the mouthpiece, an indexing mechanism adapted to engage and move the first and second supports, the indexing mechanism and the supports being configured so that in a first dispensing state of the device, the first support is in engagement with the indexing mechanism so as to be moveable with respect to the casing, and the second support is disengaged from the indexing mechanism so as to be stationary with respect to the casing, in a subsequent second dispensing state of the device, the second support is in engagement with the indexing mechanism so as to be moveable with respect to the casing, and the first support is disengaged from the indexing mechanism so as to be stationary with respect to the casing, [0008] changeover means adapted to cause the device to pass from the first dispensing state to the second dispensing state.

Such a device is known from WO-A-2005/002654.

The device disclosed in the aforementioned document comprises conduits between the housings and the mouthpiece, each conduit defining a flow path for an airstream carrying the unitary dose through inhalation by the user. The device provides for one sole conduit for each unitary dose of dry powder. In use, a user actuates the device to inhale a unitary dose of medicine in the form of dry powder through one of the conduits. Upon a subsequent actuation of the device, a new unitary dose can be inhaled through a new conduit.

Furthermore, such a device allows the dispensing of a large number of unitary doses since the unitary doses of two carriers may be dispensed successively.

With the known device, it may happen that the device jams and becomes out of order when the relative positioning of the components of the device is changed in an unexpected manner such that appropriate relative movements of the components can no longer be obtained. It is especially the case after the device has been dropped causing an offset of at least one of the components.

SUMMARY

The invention aims to solve the above mentioned problem.

To this end, according to a first aspect, the invention provides for a device of the aforementioned type wherein the changeover means are adapted to lock the second support in its stationary position while the device is in the first dispensing state, and to lock the first support in its stationary position while the device is in the second dispensing state.

Hence, the changeover means positively locks and secures the stationary support while the device is in the first and second dispensing states so as to prevent any movement of the stationary support with respect to the casing. This makes it possible to reduce the risk of an unexpected change in the relative positioning of the components. The appropriate relative movements of the components can be preserved, thereby reducing the risk of jamming.

In particular, the changeover means may be adapted to release the second support from its stationary position and to place the second support into engagement with the indexing mechanism while disengaging the first support from the indexing mechanism.

Preferably, the changeover means comprise a changeover mechanism which is arranged between the first and second supports and is moveably mounted within the casing.

In an embodiment, the changeover means may comprise first and second engaging portions provided on the first and second supports respectively, the changeover mechanism may comprise first and second engaging sections and a locking arrangement arranged to cooperate with the first and second supports so that the second engaging section engages the second engaging portion and the locking arrangement prevents the changeover mechanism from moving with respect to the casing while the device is in the first dispensing state, the first and second engaging sections engage respectively the first and second engaging portions, and the locking arrangement allows the changeover mechanism to move with respect to the casing while the first support is disengaging from the indexing mechanism, the first engaging section engages the first engaging portion, and the locking arrangement prevents the changeover mechanism from moving with respect to the casing while the device is in the second dispensing state.

With such embodiment, the switching of the locking arrangement may be achieved in an accurate manner so that the second support is released at a desired moment to enable the device to pass from the first dispensing state to the second dispensing state.

The first and second supports may comprise respectively first and second contact surfaces, and the locking arrangement may comprise first and second abutting sections arranged on the changeover mechanism to cooperate respectively with the first and second contact surfaces so that the first abutting section abuts the first contact surface while the device is in the first dispensing state, the first and second abutting sections do not abut the first and second contact surfaces while the first support is disengaging from the indexing mechanism, the second abutting section abuts the second contact surface while the device is in the second dispensing state.

The first and second supports may further comprise first and second notches arranged respectively on the first and second supports in correspondence with the first and second engaging portions, the first and second notches being adapted to remove the abutments of the first and second abutting sections on the first and second contact surfaces while the first support is disengaging from the indexing mechanism.

Preferably, the changeover mechanism is integrally made, for example as a one-piece moulded component. This results in a more compact device that is easy to manufacture.

In this example, the first and second supports may be superposed and the changeover mechanism may be rotatably mounted within the casing, the changeover mechanism having first and second sides cooperating respectively with the first and second supports.

Besides, each of the first and second engaging sections may be made of gear teeth adapted to mesh with gear teeth of each of the first and second engaging portions, and each of the first and second abutting sections may comprise surfaces angularly offset with respect to the respective first and second engaging sections.

In particular, the respective surfaces of the first and second abutting sections may be at least partly formed on the gear teeth of the first and second engaging sections.

The first and second supports may be of circular configuration, the first and second supports being rotatably mounted within the casing about a central axis.

According to a second aspect, the invention concerns an inhaler comprising a device for dispensing a plurality of unitary doses of dry powder as defined above, and two carriers each having a plurality of housings for respective unitary doses, the two carriers being associated respectively with the first and second supports.

BRIEF DESCRIPTION OF THE DRAWINGS

Other objects and advantages of the invention will emerge from the following disclosure made in reference to the enclosed drawings in which:

FIGS. 7 and 8 are views in perspective of the support partially cut and the carrier of the inhaler of FIG. 1, illustrating the assembly of the carrier and the support and two steps of a dispensing process of a unitary dose of dry powder carried by the carrier, FIG. 18 is a perspective view of the arrangement of the changeover component with respect to the first and second supports for the respective first and second carriers in the inhaler of FIG. 1, FIGS. 19a and 19b are respectively top and bottom views of the arrangement of FIG. 18 when a last unitary dose of the first carrier is dispensed, illustrating respectively the first side of the changeover component that prevents rotation of the changeover component, and the second side of the changeover component that engages the second support.

DETAILED DESCRIPTION

On the Figures, same references refer to similar or analogous elements.

Figure 1:
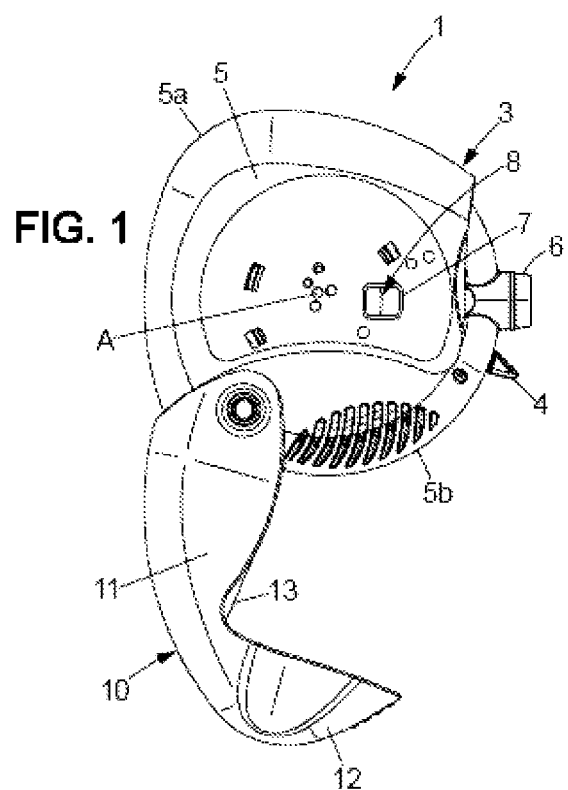
FIG. 1 is a side view of an inhaler comprising a device for dispensing a plurality of unitary doses of dry powder according to an embodiment of the invention.

FIG. 1 illustrates an inhaler 1 from which a user may inhale successively unitary doses 2 of medicament in the form of dry powder.

Figure 3:
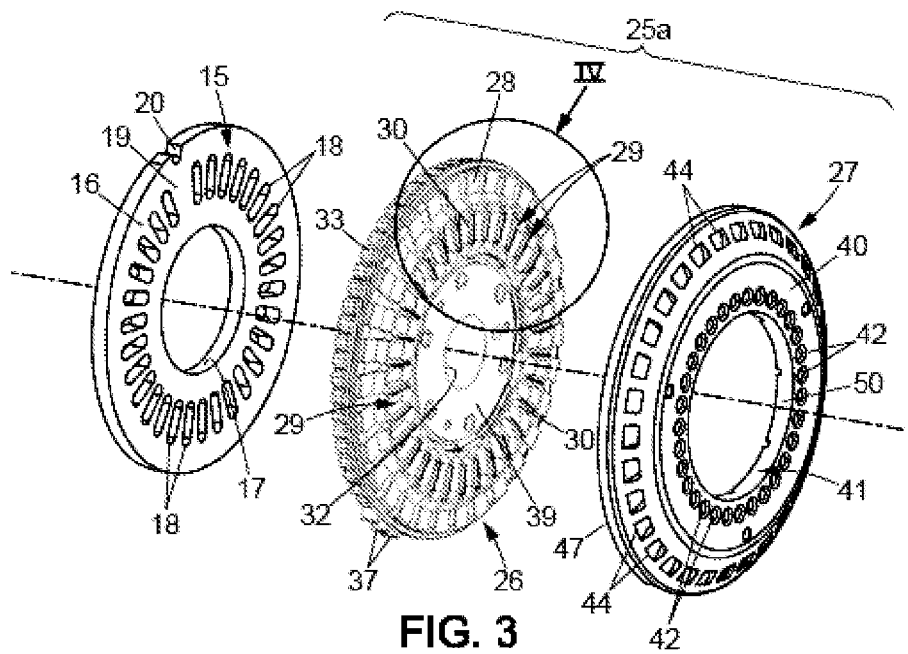
FIG. 3 is an exploded view of top faces of a support and a carrier of the inhaler of FIG. 1, illustrating top surfaces of the carrier and of an anvil plate and an airway plate forming the support.
Figure 5:
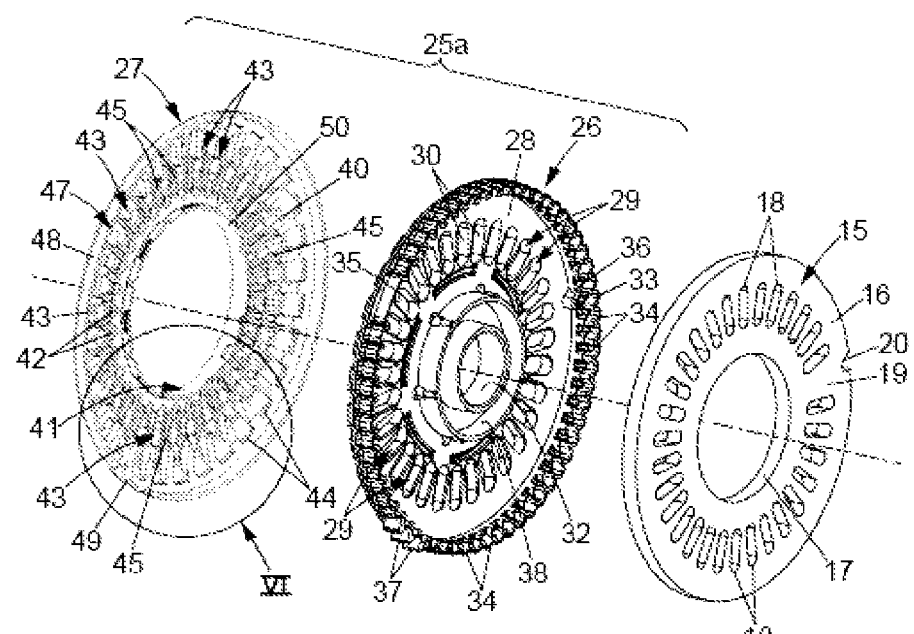
FIG. 5 is an exploded view of bottom faces of the support and the carrier of the inhaler of FIG. 1, illustrating bottom surfaces of the carrier, of the anvil plate and of the airway plate.

The inhaler 1 of the illustrated embodiment includes a device 3 for dispensing the unitary doses 2 and two carriers 15, visible in particular on FIGS. 3 and 5, which carry the unitary doses 2 and which are mounted in the device 3.

On FIG. 1, the device 3 comprises a casing 5 presenting a contour with a hump-shaped part 5a and a constant-radius shaped part 5b.

The casing 5 is provided with a mouthpiece 6, formed integrally with the casing 5 or as a separate component, arranged substantially at a first end of the constant-radius shaped part 5b.

Figure 2:
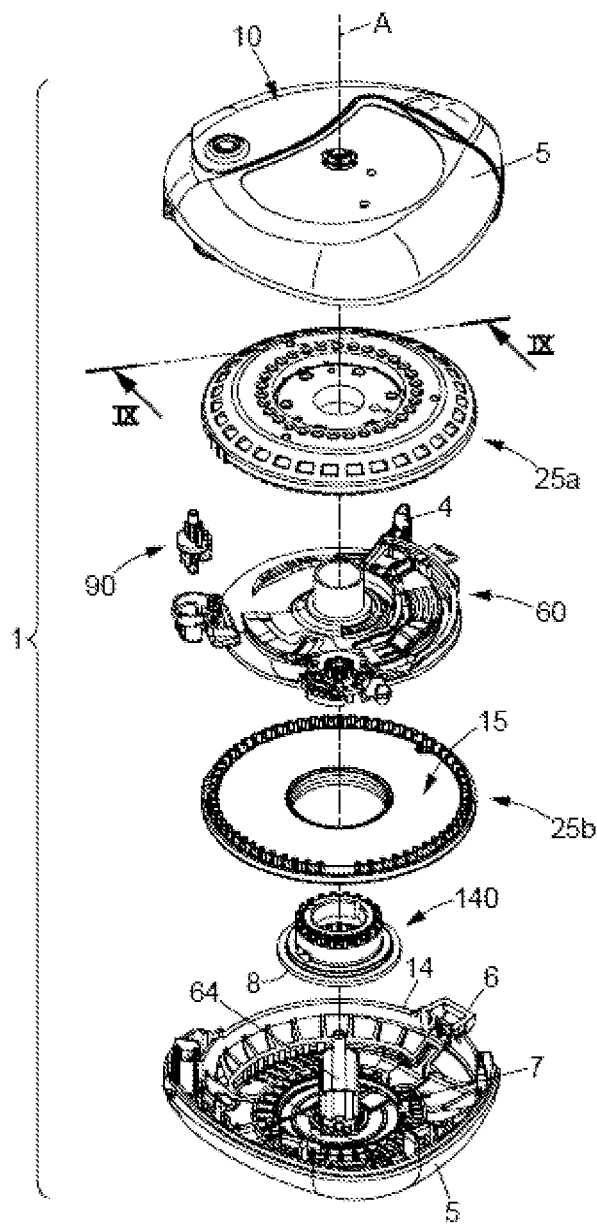
FIG. 2 is an exploded view in perspective of the inhaler of FIG. 1.

The constant-radius shaped part 5b is provided with a slot 14, partly visible on FIG. 2, extending from the mouthpiece 6 to a second end opposite to the first end. A priming lever 4 extends out of the casing 5 through the slot 14. As it will be apparent from the following description, the priming lever 4 is mounted so as to rotate around the constant-radius shaped part 5b, about a central axis A, along a stroke delimited by the slot 14. The user may actuate the priming lever 4 to prime the device 3 so that one of the unitary doses 2 may be inhaled through the mouthpiece 6.

The device 3 includes a window 7 in one side of the casing 5. The window 7 allows the user to view a counter display 8 which provides the user with an indication of how many unitary doses 2 have been dispensed and/or how many unitary doses 2 remain unused.

An L-shaped mouthpiece cover 10 may be mounted on the casing 5. The mouthpiece cover 10 comprises long 11 and short 12 hollow parts substantially perpendicular to each other. An end of the long part 11 is rotatably mounted on the casing 5 in the vicinity of the second end of the constant-radius shaped part 5b so that the long 11 and short 12 parts may selectively cover or expose, as illustrated on FIG. 1, the slot 14, the priming lever 4 and the mouthpiece 6. An actuation rib 13, the purpose of which will be explained later, extends centrally in the long part 11.

As can be seen on FIG. 2, the casing 5 is made of two halves assembled to each other to define a housing. The casing 5 comprises a central shaft 64 extending within the housing along the central axis A and on which the following components of the device 3 are mounted: [0062] first 25a and second 25b supports which each receive one respective of the carriers 15, [0063] an actuating mechanism 60 arranged between the first 25a and second 25b supports and comprising the priming lever 4, [0064] a changeover mechanism 90, and [0065] a counter mechanism 140.

With reference to FIGS. 3, 4, 5 and 6, one of the carriers 15 and the first support 25a are described, by way of example. This description can be transposed to the other carrier 15 and to the second support 25b, these being identical or at least similar to the described carrier 15 and first support 25a.

As can be seen on FIGS. 3 and 5, the carrier 15, similar to that disclosed in WO-A-2005/002654, is formed from a disc-shaped plate 16 having an axis and a central opening 17. The plate 16 is provided with a plurality of through-holes 18 extending between top and bottom surfaces of the plate 16 and defining housings for the respective unitary doses of dry powder. In the illustrated embodiment, thirty through-holes 18 are arranged at equally spaced locations, according to a circumferential array. The through-holes 18 are hence adjacent to each other in a circumferential direction and extend in radial directions with respect to the axis of the plate 16.

One location of the plate 16 is deprived of a through-hole, so that a full portion 19 is formed between two adjacent through-holes 18. An indent 20 is formed at the periphery of the plate 16 in correspondence with this full portion 19.

Each through-hole 18 may receive a cup-shaped insert 21, visible in particular on FIGS. 7 and 8, opening in the top surface of the plate 16. Each insert 21 is adapted to contain one of the unitary doses 2 of dry powder. To protect the dry powder, especially from humidity and contaminants, and to retain the inserts 21 and the dry powder in the through-holes 18, appropriate top 22 and bottom 23 lidding sheets may be secured to the top and bottom surfaces of the plate 16.

The first support 25a is of circular configuration with respect to an axis and has first and second members, consisting respectively of an anvil plate 26 and an airway plate 27.

As can be seen on FIG. 3 which shows a top surface of the anvil plate 26, the anvil plate 26 comprises a disc-shaped part 28 pierced with a central opening 32. The disc-shaped part 28 is provided with successive through-holes 29 adapted to be placed in correspondence respectively with the through-holes 18 of the carrier 15. As for the carrier 15, the though-holes 29 are adjacent to each other in a circumferential direction and extend in radial directions with respect to the axis of the first support 25a. The disc-shaped part 28 is provided with radial walls 30 each extending in a radial direction and each arranged between two adjacent through-holes 29 so as to separate them.

Figure 4:
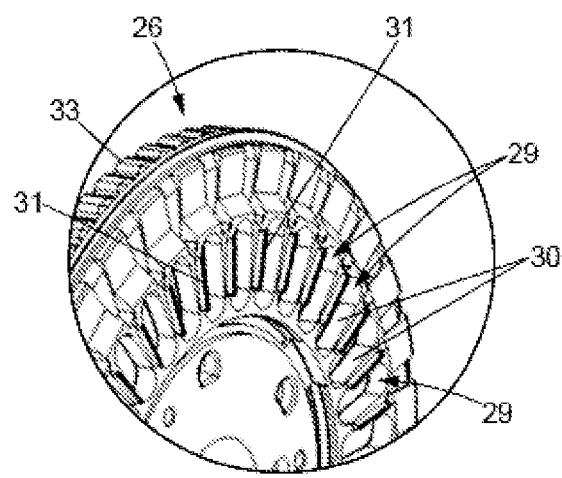
FIG. 4 is an enlarged view of the detail referenced IV on FIG. 3, illustrating a portion of the top surface of the anvil plate.

On FIG. 4, it can be seen that each radial wall 30 of the disc-shaped part 28 of the anvil plate 26 has a rib 31 protruding on the top surface of the anvil plate 26. Each rib 31 has a rectangular cross-section and a radial dimension which corresponds substantially to that of the adjacent through-holes 29.

The anvil plate 26 also has a securing element for attachment of the top surface of the anvil plate 26 to the airway plate 27. In the illustrated embodiment, a recessed portion 39 surrounding the central opening 32 is formed on the disc-shaped part 28 to cooperate with a securing element of the airway plate 27.

As can be seen on FIG. 5 which shows a bottom surface of the anvil plate 26, the anvil plate 26 is generally concave with a concavity formed on its bottom surface. For example, the anvil plate 26 is provided with an annular lateral wall 33 adapted to surround the external periphery of the carrier 15 so as to accommodate the carrier 15 in the concavity of the anvil plate 26. In particular, the lateral wall 33 extends perpendicularly to an outer edge of the disc-shaped part 28.

Internally, the lateral wall 33 is provided with a coupling portion formed, for example, of gear teeth 34 protruding toward the axis of the first support 25a, and with a decoupling portion formed, for example, of a smooth part 35 arranged locally and deprived of gear tooth. The lateral wall 33 also has a protrusion 36 extending toward the axis and adapted to be received in the indent 20 of the carrier 15.

Externally, the lateral wall 33 is provided with an engaging portion formed, for example, of gear teeth 37 arranged locally and protruding opposite to the axis.

The appropriate relative arrangement of the coupling and decoupling portions, of the protrusion 36 and of the engaging portion will become apparent from the following description of the device 3.

The anvil plate 26 also has a securing element for attachment of the carrier 15 to the bottom surface of the anvil plate 26. In the illustrated embodiment, the bottom surface comprises a mounting skirt 38 extending perpendicularly from the disc-shaped part 28 and adapted to be fitted in the central opening 17 of the carrier 15.

Regarding the airway plate 27, as can be seen on FIG. 3 which shows a top surface of the airway plate 27, it comprises a disc-shaped part 40 pierced with a central opening 41. The disc-shaped part 40 is provided with successive pairs of through-holes 42, 44 adjacent to each other in a circumferential direction. The through-holes 42, 44 of each pair of through-holes extend in a radial direction with respect to the axis of the first support 25a and are adapted to be placed in correspondence with one of the through-holes 29 of the anvil plate 26.

As can be seen on FIG. 5 which shows a bottom surface of the airway plate 27, the disc-shaped part 40 is provided with successive channels 43 and with radial walls 45 arranged so that the channels 43 and the radial walls 45 of the airway plate 27 may face respectively the through-holes 29 and the radial walls 30 of the anvil plate 26. The channels 43 are adjacent to each other in a circumferential direction. Each channel 43 extends in the radial direction between one pair of the through-holes 42, 44 so as to form an inlet 42, close to the axis of the first support 25a, and an outlet 44, at a distance from the axis of the first support 25a, for the channel 43. Each radial wall 45 extending in a radial direction is arranged between two adjacent channels 43 so as to separate them.

The airway plate 27 is generally concave with a concavity formed on its bottom surface adapted to accommodate the anvil plate 26, such that the anvil plate 26 is interposed between the airway plate 27 and the carrier 15. For example, the airway plate 27 is provided with an annular lateral wall 47 adapted to surround the lateral wall 33 of the anvil plate 26. In particular, the lateral wall 47 extends perpendicularly to an outer edge of the disc-shaped part 40. The lateral wall 47 presents an outer smooth contact surface 48 and a notch 49 extending locally from a free edge of the lateral wall 47.

In the illustrated embodiment, the securing element for attachment of the airway plate 27 to the top surface of the anvil plate 26 comprises a mounting flange 50 surrounding the central opening 41 and adapted to be fitted in the recessed portion 39 of the anvil plate 26.

Figure 6:
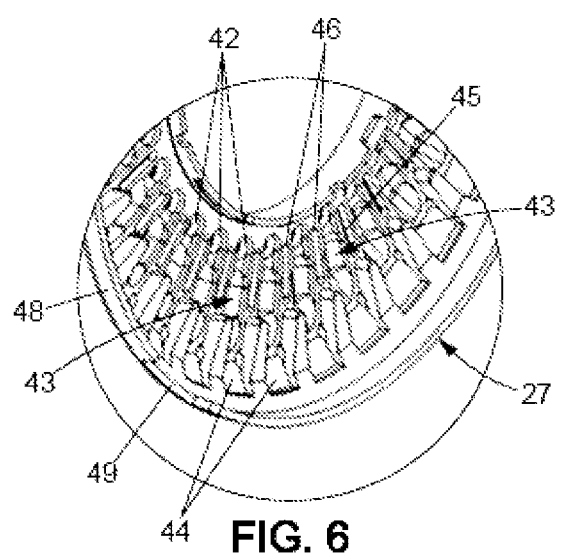
FIG. 6 is an enlarged view of the detail referenced VI on FIG. 5, illustrating a portion of the bottom surface of the airway plate.

On FIG. 6, it can be seen that each radial wall 45 of the disc-shaped part 40 of the airway plate 27 has a groove 46 formed in the bottom surface of the airway plate 27. Each groove 46 of rectangular cross-section is adapted to receive the rib 31 protruding on the corresponding radial wall 30 of the anvil plate 26.

FIG. 7 illustrates the above disclosed anvil plate 26 and airway plate 27 assembled to form the first support 25a in which one of the carrier 15 is received.

From the above, the anvil plate 26 and the airway plate 27 are secured to one another with the bottom surface of the airway plate 27 in contact with the top surface of the anvil plate 26, and the mounting flange 50 of the airway plate 27 fitted in the recessed portion 39 of the anvil plate 26. The lateral wall 47 of the airway plate 27 surrounds the lateral wall 33 of the anvil plate 26. As apparent from FIG. 2, the gear teeth 37 of the engaging portion of the anvil plate 26 extend in the notch 49 of the airway plate 27.

The channels 43 of the airway plate 27 are in communication respectively with the through-holes 29 of the anvil plate 26. In particular, the inlet 42 of each channel 43 communicates with one side of its corresponding through-hole 29 whilst the outlet 44 communicates with the opposite side of the corresponding through-hole 29.

The through-holes 29 of the anvil plate 26 and the channels 43 of the airway plate 27 form respectively first and second conduit portions which together define a plurality of conduits adapted to be connected respectively to the housings of the carrier 15. The conduits are adjacent to each other in the circumferential direction and extend in radial directions with respect to the support 25. The radial walls 30 of the anvil plate 26 and the radial walls 45 of the airway plate 27 form respectively first and second separation portions interposed between the conduits.

The carrier 15 is mounted within the first support 25a with the top lidding sheet 22 in contact with the bottom surface of the anvil plate 26, and the central opening 17 of the carrier 15 fitted on the mounting skirt 38 of the anvil plate 26. The lateral wall 33 of the anvil plate 26 surrounds the periphery of the carrier 15 with the protrusion 36 of the anvil plate 26 placed in the indent 20 of the carrier 15, thereby providing an appropriate positioning of the through-holes 18 and the full portion 19 of the carrier 15 with respect to the conduits of the first support 25a. In this regard, it will be appreciated that each housing of the carrier 15 has its own conduit formed in the first support 25a, the conduit being adapted to define a flow path for an airstream carrying the unitary dose through inhalation by a user.

In relation to FIGS. 7 and 8, a dispensing process of one of the unitary doses 2 of dry powder contained in one insert 21 is disclosed.

On FIG. 7, the insert 21 is in a storage position in which it is fully contained in the through-hole 18 of the carrier 15 and flush with the top surface of the carrier 15. The insert 21 faces the conduit of the first support 25a.

As shown on FIG. 8, by pushing the insert 21 from the side of the bottom lidding sheet 23, it is possible to move the insert 21 outwardly to a discharge position, in which the insert 21 protrudes from the top surface of the carrier 15 and extends in the through-hole 29 of the anvil plate 26. The insert 21 used to outwardly burst through the top lidding sheet 22 is still held securely in place. In this respect, the anvil plate 26 can be used to improve the predictability of the rupture of the top lidding sheet 22.

In the discharge position, the insert 21 within the conduit faces the inlet 42 of the channel 43. In this way, when the user inhales through the mouthpiece 6 of the device 3, an airstream, illustrated by an arrow on FIG. 8, may be drawn through the airway plate 27 such that it passes through the inlet 42 down into the insert 21, back up into the channel 43 and then out of the outlet 44. The unitary dose of dry powder in the insert 21 is thus picked up by the airstream, removed from the insert 21 and carried out of the first support 25a.

Suitable dimensions and shape of the conduits to ensure the dry powder is picked up, and where needed deaggregated, may resume that disclosed in WO-A-2005/002654. Besides, as in WO-A-2005/002654, a second flow path which bypasses the insert 21 may be provided to increase the overall cross sectional area available through which to inhale, and to control the overall flow resistance of the device so that it is comfortable for the user to inhale through. This second flow path may be formed by walls of the casing 5.

Figure 9:
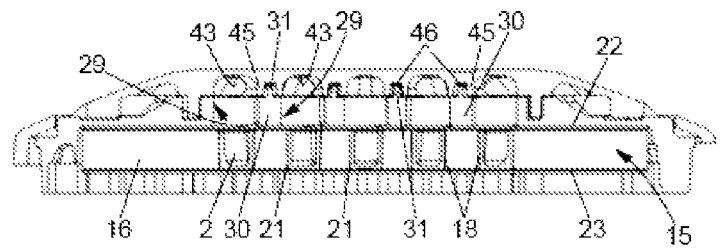
FIG. 9 is a view in section along line referenced IX-IX on FIG. 2 of the support and the carrier of the inhaler of FIG. 1, illustrating barrier-forming elements at an interface between the anvil plate and the airway plate.

As can be seen on FIG. 9, in the first support 25a, when the anvil plate 26 and the airway plate 27 are assembled, the ribs 31 on the radial walls 30 of the anvil plate 26 are placed within the grooves 46 of the radial walls 45 of the airway plate 27.

Therefore, even if small gaps exist at the interface between the radial walls 30, 45 delimiting respectively the through-holes 29 of the anvil plate 26 and the channels 43 of the airway plates 27, for example because these radial walls 30, 45 are not closely tightened, the arrangement of ribs 31 and grooves 46 provides a circuitous path between two adjacent conduits.

In the case where the first and second unitary doses 2 of dry powder are placed in communication respectively with adjacent first and second conduits, the airstream created in the second conduit through inhalation by the user to pick up the second unitary dose 2 will draw the dry powder of the second unitary dose 2 without drawing that of the first unitary dose since the arrangement of rib 31 and groove 46 between corresponding radial walls 30, 45 of the anvil plate 26 and of the airway plate 27 inhibits dry powder of the first unitary dose 2 from passing from the first conduit to the adjacent second conduit.

This situation may arise when the user actuates the device, thereby moving the insert 21 containing the first unitary dose 2 in the discharge position, and is distracted before inhaling the first unitary dose 2. Subsequently, the user actuates the device once again, forgetting that he actuated it previously, thereby moving the insert 21 containing the second unitary dose 2 into the discharge position.

The rib 31 and the groove 46 of two facing radial walls of the anvil plate 26 and the airway plate 27 form barriers to the dry powder of the adjacent conduits, limiting thereby cross-dosing, i.e. the amount of dry powder inhaled when the previous unitary dose has been missed or untaken.

For example, in the device disclosed in WO-2005/002654 deprived of barrier-forming elements such as the above described rib and groove arrangement, it has been found that the cross-dosing could reach 150% or more of the nominal unitary dose, that is an excess of 50% or more of dry powder of the previous unitary dose may be inhaled when the subsequent unitary dose is inhaled.

The use of barrier-forming elements aims to reduce cross-dosing to 135% or less. In particular, a cross-dosing of less than 115% can be obtained with the barrier-forming elements.

Of course, the barrier-forming elements are not limited to the above described rib and groove arrangement. For example, the ribs 31 could be arranged on the airway plate 27 and the grooves 46 could be arranged on the anvil plate 26.

Besides, in the above described embodiment, the barrier-forming elements form a baffle between the corresponding radial walls 30, 45 of the anvil plate 26 and the airway plate 27 providing a circuitous path between two adjacent conduits. Therefore, the barrier-forming elements may comprise any angled or curved interface between the corresponding walls 30, 45 of the anvil plate 26 and the airway plate 27.

In particular, the barrier-forming elements may comprise more than one rib 31 and one groove 46.

Figure 10:
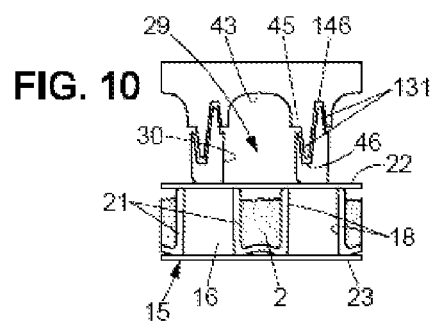
FIGS. 10, 11 and 12 are enlarged views of alternative embodiments of the barrier-forming elements at the interface between the anvil plate and the airway plate.

For example, as illustrated on FIG. 10, each radial wall 30 of the anvil plate 26 is provided with one radial rib 131 and one radial groove 146 adapted to cooperate respectively with one radial groove 146 and one radial rib 131 of the corresponding radial wall 45 of the airway plate 27. Besides, on FIG. 10, each rib 131 includes a first pair of opposed surfaces inclined with respect to one another, and each groove 146 includes a second pair of opposed surfaces inclined with respect to one another and complementary to the first pair of opposed surfaces of the corresponding rib 131.

Figure 11:
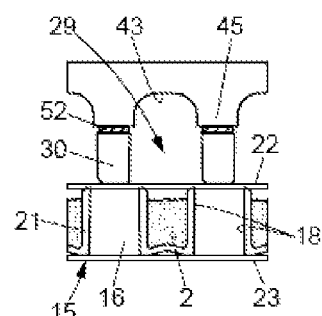

FIG. 11 illustrates an alternative embodiment of the barrier-forming elements in which an additive layer 52 is interposed between the corresponding radial walls 30, 45 of the anvil plate 26 and the airway plate 27. Any appropriate gasket or adhesive in any appropriate pattern, such as continuous layers, discrete points or other, could be used as additive layer.

Figure 12:
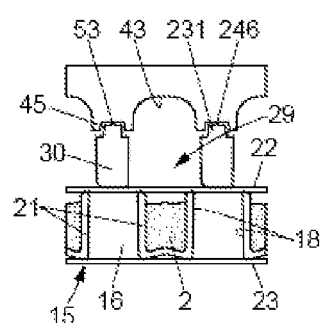

Besides, as shown on FIG. 12, in another alternative embodiment, the barrier-forming elements may comprise a welded connection between the corresponding radial walls 30, 45 of the anvil plate 26 and the airway plate 27. In this embodiment, the radial walls of the anvil plate 26 and the airway plate 27, or the anvil plate 26 and the airway plate 27 themselves, are made of thermoplastic material and are configured to permit the corresponding radial walls 30, 45 to be joined by an ultrasonic welding process. For example, a tipped protrusion or energy director 53 is arranged on the rib 231 and abuts the bottom surface of the groove 246. The relative movement of the anvil plate 26 and the airway plate 27 caused by ultrasonic vibrations will cause the thermoplastic material to melt and the radial walls 30, 45 to be welded.

The barrier-forming elements may implement one of the above disclosed embodiments or may combine several of them.

As can be seen on FIG. 2, within the casing 5, the first 25a and second 25b supports with their respective carriers 15 are superposed and arranged coaxially to the central axis A, the bottom surfaces of the carriers 15 facing each other. The first 25a and second 25b supports are rotatably mounted within the casing 5 about the central axis A so as to bring successively each conduit in communication with the mouthpiece 6, thus sequentially connecting the housings to the mouthpiece.

Figure 13:
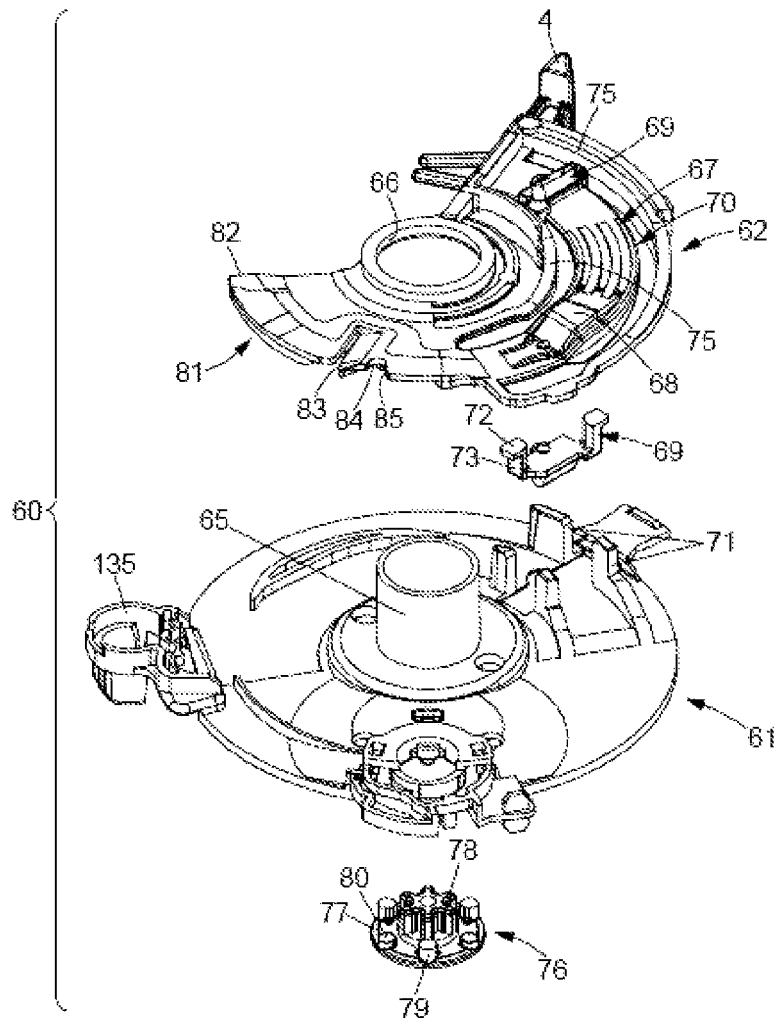
FIG. 13 is an exploded view of an actuating mechanism of the inhaler of FIG. 1.

The actuating mechanism 60, illustrated in detail on FIG. 13, is arranged between the bottom surfaces of the carriers 15. The actuating mechanism 60 is adapted to expose one of the unitary doses 2 of dry powder such that it may be carried with the airstream out of the mouthpiece 6 each time the priming lever 4 is actuated.

In particular, the actuating mechanism 60 comprises a dispensing mechanism adapted to expose each unitary dose 2 to the corresponding conduit, and an indexing mechanism adapted to place each conduit in communication with the mouthpiece 6.

The actuating mechanism 60 comprises a disc-shaped chassis 61 which supports the dispensing mechanism and the indexing mechanism. The chassis is fixed to the casing 5 and comprises a hollow pivot shaft 65 fitted on the shaft 64 of the casing 5. At a location, the chassis comprises guide members 71 extending axially and defining a radial aperture between them.

The actuating mechanism 60 further comprises a priming member 62 bearing the priming lever 4 and rotatable about the central axis A so as to operate the dispensing mechanism and the indexing mechanism when the priming lever 4 is actuated.

An example of a suitable priming member 62 is disclosed in WO-A-2005/002654. The priming member 62 is formed of a disc-shaped plate moulded in plastic and having a central pivot opening 66 by which it is rotatably supported on the pivot shaft 65 of the chassis 61.

In the illustrated embodiment, the dispensing mechanism is adapted to move each insert 21 of each carrier 15 from its storage position to its discharge position. Again, an example of a suitable dispensing mechanism, implementing prodgers 69 mounted on the priming member 62, and cam surfaces 68, 75 arranged on the priming member 62 and adapted to move the prodgers 69 axially, is disclosed in WO-A-2005/002654.

In particular, the dispensing mechanism includes an elongate cam member 67 formed on the priming member 62 and separated from the remaining part of the priming member 62 by elongate openings 70 through which the abutment members 71 of the chassis 61 extend. The cam member 67 extends in a circumferential direction and presents a profile adapted to provide a limited amount of flexibility. The central cam surface 68 is provided on each of two opposite sides of the cam member 67. Besides, the lateral cam surfaces 75 extend on either side of the priming member 62, in circumferential directions along the elongate openings 70, opposite the cam member 67.

The prodgers 69 are identical to each other and clip together with the cam member 67 between them. Each prodger 69 has arms 73 extending perpendicularly to a central part arranged to cooperate with the central cam surface 68 of the cam member 67. The arms 73 extend through the elongate openings 70 of the priming member 62, and have features 72 arranged at their ends to contact the lateral cam surfaces 75 of the priming member 62.

The elongate openings 70 of the priming member 62 and the guide members 71 on the chassis 61 are arranged to hold the prodgers 69 rotationally but to allow them to move in an axial direction of the device 3, towards and away from the carriers 15 by means of the central 68 and lateral 75 cam surfaces that positively guide the prodgers 69.

As explained in WO-A-2005/002654, the actuating mechanism 60 arranges for one of the prodger 69 to be in alignment with one of the insert 21 of the corresponding carrier 15 while the other prodger 69 faces the full portion 19 of the other carrier 15. In this way, the dispensing mechanism only dispenses one unitary dose 2 of one of the carrier 15 at a time.

Operation of the dispensing mechanism is now described.

Movement of the priming lever 4 in the slot 14 of the casing 5 along its stroke from a first position close to the mouthpiece 6 to a second position at a distance from the mouthpiece 6 primes the device 3 to expose the unitary dose 2 of dry powder to the corresponding conduit.

At an initial step, when the user moves the mouthpiece cover 10 to expose the mouthpiece 6, the priming lever 4 is in its first position and both prodgers 69 are in a retracted position at one end of the cam member 67 opposite the central cam surfaces 68.

When the user moves the priming lever 4 to its second position, the priming member 62 is rotated relative to the chassis 61. The cam surfaces 68 of the cam member 67 engage the prodgers 69, respectively. The cam surface 68 that engages the prodger 69 in alignment with one of the insert 21 presses out this prodger 69 so that this prodger 69 is moved outwardly towards its corresponding carrier 15, penetrates the through-hole 18 of the carrier 15 and pushes the insert 21 in the discharge position. Meanwhile, the cam surface 68 that engages the prodger 69 in alignment with the full portion 19 deforms thanks to its flexibility.

After the user has inhaled the unitary dose 2, the mouthpiece cover 10 may be rotated back by the user. The actuation rib 13 of the mouthpiece cover 10 may engage the priming lever 4 to move it back to its first position. The lateral cam surfaces 75 of the priming member 62 retract the prodgers 69.

The indexing mechanism will now be described.

In the illustrated embodiment, the indexing mechanism is adapted to move the first 25*a* and second 25*b* supports in successive active positions in each of which one of the conduits is connected to the mouthpiece 6 so that the corresponding unitary dose 2 may be carried by the airstream through the mouthpiece 6. An example of a suitable indexing mechanism implementing an intermittent motion mechanism is disclosed in WO-A-2005/002654.

In particular, the indexing mechanism comprises a Geneva wheel 76 rotatably mounted within the casing 5 about an axis parallel to the central axis A. The Geneva wheel 76 includes a peg wheel 77 adapted to cooperate with the priming member 62 so that the Geneva wheel rotates through an angle of 120.degree. each time the priming lever 4 is actuated. The Geneva wheel 76 also includes two gears 78 coaxial with the peg wheel 77 and adapted to cooperate respectively with the coupling portions of the first 25*a* and second 25*b* supports.

The peg wheel 77 has three long pegs 79 and three short pegs 80 arranged alternately at intervals of 60.degree. around its edge.

The indexing mechanism further comprises a driving member 81 formed on an outer edge of the priming member 62. The driving member 81 is arranged so that:

when the priming lever 4 is moved from its first position to its second position so that, as explained above, the dispensing mechanism pushes the insert 21 in the discharge position, the driving member 81 does not rotate the Geneva wheel 76, when the priming lever 4 is moved back from its second position to its first position, the driving member 81 rotates the Geneva wheel 76.

In particular, the driving member 81 is placed, in the circumferential direction, next to a portion of the priming member 62 comprising the dispensing mechanism.

The driving member 81 is provided with a leading portion 82, a ratchet pawl 83 which slopes downward toward the leading portion 82, and a slot 84 with a trailing edge 85 arranged in sequence.

The operation of the indexing mechanism will now be described in relation to one cycle defined by the movement of the priming lever 4 as it is actuated by the user. The terms "first", "second" and "third" related to the long 79 and short 80 pegs in the following description are used in relation to one cycle. It should be understood that the "first", "second" and "third" pegs would change in a subsequent cycle.

As indicated above, when the priming lever 4 is moved from its first position to its second position, the driving member 81 does not rotate the Geneva wheel 76. In particular, the peg wheel 77 and the driving member 81 are arranged so that the outer edge of the priming member 62 passes over the first of the short pegs 80 and slides against the first and second of the long pegs 79 adjacent on either side of the first short peg 80, the ratchet pawl 83 deforming when passing over the second short peg 80. The peg wheel 76 is therefore prevented from rotating.

When the priming lever 4 returns from its second position to its first position, the leading portion 82 passes over the first short peg 80 and the outer edge of the priming member 62 slides against the first and second long pegs 79, thereby preventing the peg wheel 77 from rotating. Then the ratchet pawl 83 engages with the first short peg 80 so that the peg wheel 77 is driven around, the second long peg 79 entering the slot 84. As the ratchet pawl 83 disengages the first short peg 80, the trailing edge 85 of the slot 84 engages the second long peg 79 and continues to drive the peg wheel 77 around. As the trailing edge 85 of the slot 84 disengages the second long peg 79, the outer edge of the priming member 62 passes over the second of the short pegs 80 adjacent to the second long peg 79 and abuts against the second and third of the long pegs 79.

The indexing mechanism causes one of each carrier 15 to be incremented by one unitary dose 2 each time the priming lever 4 is actuated.

The gear teeth 34 of the coupling portion of each airway plate 27 may be in engagement with the corresponding gear 78 of the Geneva wheel 76 so as to be moved with respect to the casing 5 successively in the active positions. The numbers of gear teeth 34 on the airway plates 27 and gears 78 are arranged so that the motion of an angle of 120.degree. of the Geneva wheel 76 increments the support 25 exactly one conduit pitch.

Therefore, the indexing mechanism rotates successively each support 25 to the next position in which one of the conduits is in communication with the mouthpiece 6 and the prodger 69 is aligned with a new insert 21. The above described operation of dispensing the unitary dose can then be repeated.

To avoid having both first 25*a* and second 25*b* supports driven simultaneously, the indexing mechanism is caused initially to drive the first support 25*a* and, when this has had all of its unitary doses 2 dispensed, to then drive the second support 25*b*.

The first 25*a* and second 25*b* supports are configured, in particular through the appropriate relative arrangement of the coupling and decoupling portions, of the protrusions 36 and of the engaging portions of the first 25*a* and second 25*b* supports, so that the device 3 presents:

a first dispensing state, in which the first support 25*a* is in engagement with the Geneva wheel 76 of the indexing mechanism so as to be moved with respect to the casing 5 in each active position, and the second support 25*b* is disengaged from the Geneva wheel 76 of the indexing mechanism so as to be stationary with respect to the casing 5, a subsequent second dispensing state, in which the second support 25*b* is in engagement with the Geneva wheel 76 of the indexing mechanism so as to be moveable with respect to the casing 5 in each active position, and the first support 25*a* is disengaged from the Geneva wheel 76 of the indexing mechanism so as to be stationary with respect to the casing 5.

In this respect, it is arranged that the decoupling portion of the airway plate 27 of one of the first 25*a* and second 25*b* supports faces the corresponding gear 78 of the Geneva wheel 76, while the gear teeth 34 of the coupling portion of the airway plate 27 of the other of the first 25*a* and second 25*b* supports engage the corresponding gear 78 of the Geneva wheel 76. As a result, with its decoupling portion, the airway plate 27 may be disengaged from the gear 78 of the Geneva wheel 76 so that rotation of the Geneva wheel 76 does not rotate the support 25.

Besides, the decoupling portion and the protrusion 36 of each of the first 25a and second 25b supports are arranged so that when the decoupling portion faces the gear 78 of the Geneva wheel 76, the prodger 69 faces the full portion 19 of the carrier 15 and no unitary dose of this carrier 15 can be dispensed. Thus, as the indexing mechanism drives the first support 25a, in the first dispensing state of the device 3, the second support 25b remains stationary with respect to the casing 5, in an inactive position in which there is no connection between any unitary dose of the carrier 15 of this second support 25b and the mouthpiece 6. And subsequently, as the indexing mechanism drives the second support 25b, in the second dispensing state of the device 3, the first support 25a remains stationary with respect to the casing 5, in an inactive position in which there is no connection between any unitary dose of the carrier 15 of this first support 25a and the mouthpiece 6.

The embodiment described above is arranged to dispense the dry powder from each insert 21 of one carrier 15 and then subsequently the dry powder from each insert 21 of the other carrier 15.

FIGS. 14, 15, 16 and 17 illustrate the changeover mechanism 90 provided to cause the device 3 to pass from the first dispensing state to the second dispensing state.

In the illustrated embodiment, the changeover mechanism 90 is formed of an integral changeover component 91, made in one piece, for example by moulding, having first 92 and second 93 sides that extend along an axis in opposite directions from a plate 94.

Figure 14:
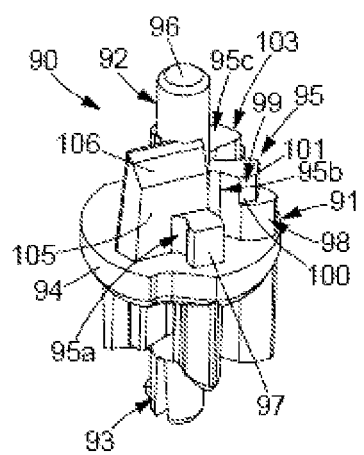
FIG. 14 is a perspective view of a changeover component of the inhaler of FIG. 1, illustrating a set of operational features on a first side of the changeover component.
Figure 15:
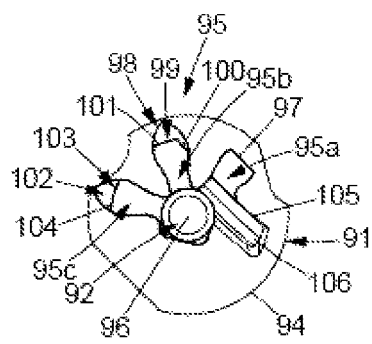
FIG. 15 is a top view of the first side of the changeover component of FIG. 14.

On FIGS. 14 and 15, the first side 92 of the changeover component 91 comprises an axle 96 and a first engaging section 95 formed, in the illustrated embodiment, of first 95a, second 95b and third 95c gear teeth arranged in sequence along an arc.

The first gear tooth 95a extends from the axle 96 in a radial direction to a free end that presents an end surface 97 substantially perpendicular to the radial direction of the first gear tooth 95a. The first gear tooth 95a has thus a limited length in the radial direction with respect to that of the second 95b and third 95c gear teeth. Besides, the first gear tooth 95a has a height along the axis of about one half of that of the second 95b and third 95c gear teeth.

The second gear tooth 95b extends from the axle 96 in a radial direction to a free end presenting a lower engaging profile 98, close to the plate 94, of a height substantially similar to that of the first gear tooth 95a, and an upper profile 99. The upper profile 99 comprises two end surfaces angled with respect to each other, one first 100 substantially parallel to the end surface 97 of the first gear tooth 95a and offset toward the axle 96 with respect to this end surface 97, the other second 101 substantially perpendicular to the radial direction of the second gear tooth 95b.

In a similar manner, the third gear tooth 95c extends from the axle 96 in a radial direction to a free end presenting a lower engaging profile 102, close to the plate 94, of a height substantially similar to that of the first gear tooth 95a, and an upper profile 103 presenting an end surface 104 substantially perpendicular to the radial direction of the third gear tooth 95c.

The first side 92 of the changeover component 91 further comprises a tab 106 extending substantially perpendicularly to the first gear tooth 95a and tangentially to the axle 96, in a direction opposite to the engaging section 95. The tab 106 presents a first abutting surface 105 substantially in alignment with the first end surface 100 of the second gear tooth 95b.

Figure 16:
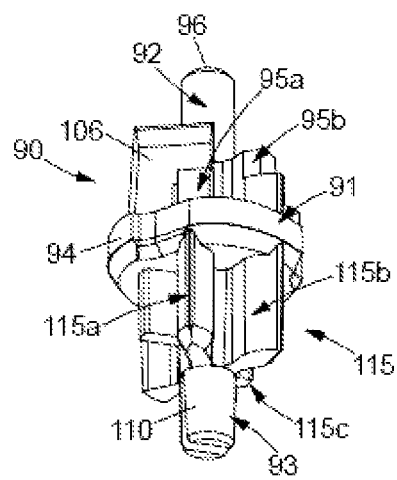
FIG. 16 is a perspective view of the changeover component of the inhaler of FIG. 1, illustrating a set of operational features on a second side of the changeover component.
Figure 17:
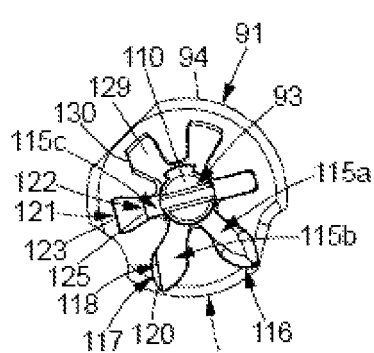
FIG. 17 is a bottom view of the second side of the changeover component of FIG. 16.

On FIGS. 16 and 17, the second side 93 of the changeover component 91 comprises an axle 110 and a second engaging section 115 formed, in the illustrated embodiment, of first 115a, second 115b and third 115c gear teeth arranged in sequence along an arc. As can be seen on FIGS. 14 and 16, the first 115a, second 115b and third 115c gear teeth of the second side 93 are substantially axially aligned respectively with the first 95a, second 95b and third 95c gear teeth of the first side 92.

The first gear tooth 115a extends from the axle 110 in a radial direction to a free end that presents an engaging profile 116.

The second gear tooth 115b extends from the axle 110 in a radial direction to a free end presenting a lower engaging profile 117, close to the plate 94, and an upper profile 118. The upper profile 118 has an end surface 120 substantially perpendicular to a radial direction along which the third gear tooth 115c extends.

The third gear tooth 115c extends from the axle 110 to a free end presenting a lower profile 121, close to the plate 94, and an upper profile 122. The lower profile 121 presents an end surface 123 substantially perpendicular to the radial direction of the third gear tooth 115c. The upper profile 122 also presents an end surface 125 substantially perpendicular to the radial direction of the third gear tooth 115c, the end surface 125 of the upper profile 122 being offset toward the axle 110 with respect to that of the lower profile 121 and being in alignment with the end surface 120 of the upper profile 118 of the second gear teeth 115b.

The second side 93 of the changeover component 91 further comprises a tab 129 extending from the axle 110 next to the third gear tooth 115c in a radial direction. The tab 129 presents a second abutting surface 130 substantially in alignment with the end surfaces 120, 125 of the upper profiles 118, 122 of the second 115b and third 115c gear teeth.

As can be seen on FIG. 18, the changeover component 91 is arranged between the first 25a and second 25b supports and rotatably mounted within the casing 5 with its axis parallel to the central axis A. For example, a casing 135, visible on FIG. 13, may be formed in one piece with the chassis 61 of the actuating mechanism to rotatably support the changeover component 91.

The first 92 and second 93 sides of the changeover component 91 cooperate respectively with the first 25a and second 25b supports.

In particular, the gear teeth 95a, 95b, and 95c of the first side 92 of the changeover component 91 are adapted to mesh with the gear teeth 37 of the engaging portion of the first support 25a. And the gear teeth 115a, 115b, and 115c of the second side 93 of the changeover component 91 are adapted to mesh with the gear teeth 37 of the engaging portion of the second support 25b.

The engaging portion of the first support 25a is arranged so as to engage the engaging section of the first side 92 of the changeover component 91 after the last unitary dose 2 of the first support 25a has been dispensed and while the first support 25a is disengaging from the indexing mechanism, i.e. the indexing mechanism moves the first support 25a so as to disengage its coupling portion and to face its decoupling portion. The engaging portion of the first support 25a remains engaged with the engaging section of the first side 92 of the changeover component 91 in the second dispensing state of the device. And the engaging portion of the second support 25b is arranged so as to engage the engaging section of the second side 93 of the changeover component 91 after the last unitary dose 2 of the first support 25a has been dispensed and while the first support 25a is disengaging from the indexing mechanism. The engaging portion of the second support 25 is engaged with the engaging section of the second side 93 of the changeover component 91 in the first dispensing state of the device.

The changeover component 91 is therefore adapted to place the gear teeth 34 of the coupling portion of the second support 25b into engagement with the corresponding gear 78 of the indexing mechanism while the other gear 78 of the indexing mechanism moves the first support 25a so as to face its decoupling portion, thereby disengaging the first support 25a from the indexing mechanism.

Furthermore, the first end surface 100 borne by the second gear tooth 95b and the first abutting surface 105 of the tab 106 of the first side 92 of the changeover component 91 form a first abutting section adapted to cooperate with the contact surface 48 of the first support 25a. And the end surfaces 120, 125 borne by the second 115b and third 115c gear teeth and the second abutting surface 130 of the tab 129 of the second side 92 of the changeover component 91 form a second abutting section adapted to cooperate with the contact surface 48 of the second support 25b.

The abutting sections of the first and second sides are arranged at opposite location with respect to the corresponding first 95 and second 115 engaging sections, whereas first 95 and second 115 engaging sections are arranged at a same location. Reasons of such arrangement will become apparent from the following description of the operation of the changeover component 91.

The description of this operation is now made in relation to FIGS. 19a, 19b, 20a, 20b, 21a and 21b.

Figure 19A:
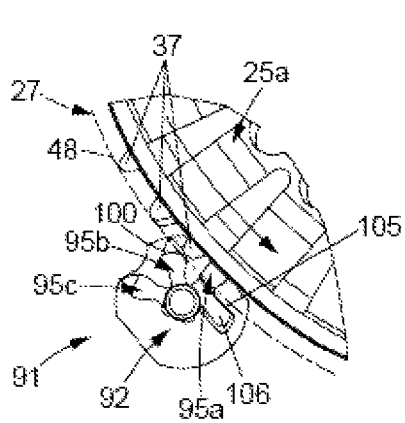

On FIG. 19a, in the first dispensing state of the device, whilst the first support 25a is in engagement with the indexing mechanism, the gear 78 of the Geneva wheel 76 meshing with the coupling portion of the first support 25a, the first support 25a is rotated, as shown by an arrow, successively in the active positions so that the unitary doses of the carrier 15 mounted in the first support 25a may be dispensed. Meanwhile, the second support 25b is locked in the inactive position.

Actually, until the first support 25a has reached last active position, the changeover component 91 is prevented from rotating because the first end surface 100 of the second gear tooth 95b and the first abutting surface 105 of the tab 106 of the first side 92 abut the contact surface 48 of the first support 25a, shown in chain dotted line. Thanks to the limited length and height of the first tooth 95a and to the limited length of the upper profile of second tooth 95b, these first 95a and second 95b teeth do not interfere with the first support 25a.

Figure 19B:
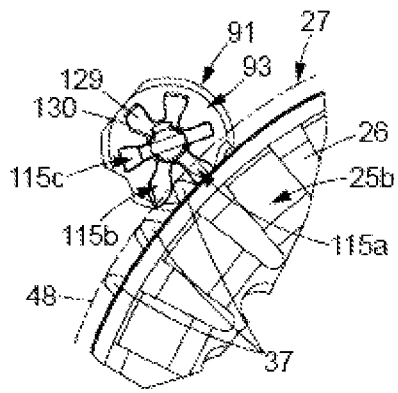

On FIG. 19b, at this same step, the first 115a and second 115b gear teeth of the second side 93 of the changeover component 91 meshes with gear teeth 37 of the engaging portion of the second support 25 through the notch 49. Since the changeover component 91 cannot rotate, the second support 25b is also prevented from rotating.

Figure 20A:
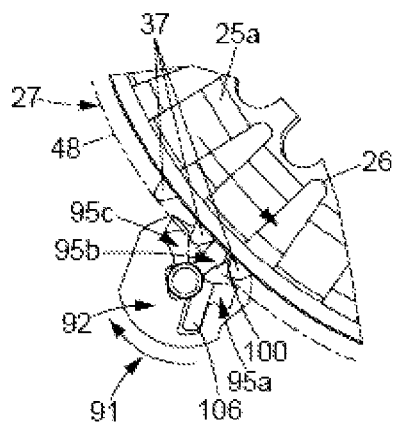
FIGS. 20a and 20b are respectively top and bottom views of the arrangement of FIG. 18 after the last unitary dose of the first carrier has been dispensed, illustrating the first support which moves the second support through the changeover component.

On FIG. 20a, after the last active position has been indexed on the first support 25a and the last unitary dose 2 has been dispensed, the indexing mechanism moves the first support 25a so that the first support 25a disengages the indexing mechanism, the decoupling portion 35 being brought in correspondence with the gear 78 of the Geneva wheel 76. The first support 25a is driven to the inactive position. At the same time, thanks to the appropriate positioning of the decoupling portion 35 and the engaging portion, the notch 49 of the first support 25a faces the first end surface 100 of the second gear tooth 95b of the first side 92 of the changeover component 91, thereby removing the rotational constraint on the changeover component 91 which can rotate.

At this step, the gear teeth 37 of the engaging portion of the first support 25a that protrude into the notch 49 mesh with the engaging profile of the first gear tooth 95a arranged in the path of the engaging portion of the first support 25a. While the first support 25a keeps on rotating to the inactive position by means of the indexing mechanism, the gear teeth 37 of the engaging portion of the first support 25a which mesh with the engaging section 95 of the first side 92 of the changeover component 91 rotate the changeover component 91 as shown by an arrow.

Figure 20B:
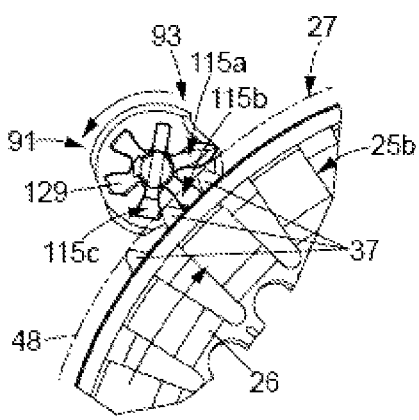

On FIG. 20b, since the changeover component 91 is now free to rotate, the gear teeth 115a, 115b and 115c of the second side 93 of the changeover component 91 that mesh with gear teeth 37 of the engaging portion of the second support 25b rotate this second support 25b, as shown by an arrow, to space apart its decoupling portion and to place its coupling portion in engagement with the corresponding gear 78 of the indexing mechanism. Thereby, the second support 25b is spaced apart from its inactive position and can be driven to a first active position by the indexing mechanism.

Figure 21A:
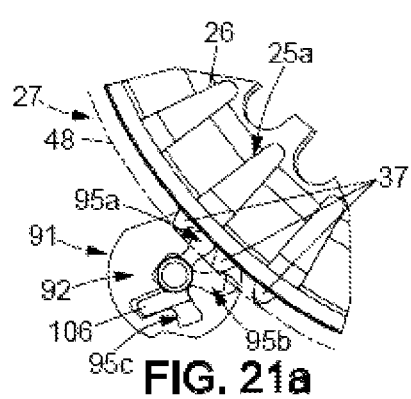
FIGS. 21a and 21b are respectively top and bottom views of the arrangement of FIG. 18 when a first unitary dose of the second carrier is dispensed, illustrating respectively the second side of the changeover component that prevents rotation of the changeover component, and the first side of the changeover component that engages the first support.
Figure 21B:
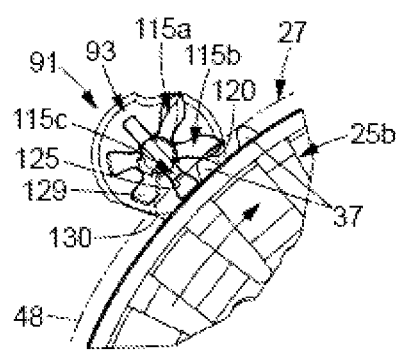

On FIG. 21b, at the completion of the move illustrated on FIG. 20b, the device is in the second dispensing state. The gear teeth 115a, 115b and 115c of the second side 93 of the changeover component 91 run out of engagement with the gear teeth 37 of the engaging portion of the second support 25b so that subsequent rotational movement of the second support 25b is independent of the changeover component 91.

On the next index and all subsequent indexes of the second support 25, the changeover component 91 is prevented from rotating because the end surfaces 120, 125 of the second 115b and third 115c gear teeth and the second abutting surface 130 of the tab 129 of the second side 93 of the changeover component 91 abut the contact surface 48 of the second support 25b, shown in chain dotted line.

On FIG. 21a, at this step, the third gear teeth 95c of the first side 92 of the changeover component 91 remains in mesh with the gear teeth 37 of the engaging portion of the first support 25a, thereby preventing this first support 25a from rotating.

Therefore, in the illustrated embodiment, the first and second abutting sections provide the changeover component 91 with a locking arrangement that:

in the first dispensing state of the device 3, prevents the changeover component 91 from rotating with respect to the casing 5 so that the changeover component 91 locks the second support 25b while the first support 25a is driven by the indexing mechanism successively between its first and last active positions to dispense the unitary doses 2 of its carrier 15, [0177] while the first support 25a is disengaging from the indexing mechanism, allows the changeover component 91 to rotate with respect to the casing 5 so that the changeover component 91 releases the second support 25b and places the second support 25b into engagement with the indexing mechanism, [0178] in the second dispensing state of the device, prevents the changeover component 91 from rotating with respect to the casing 5 so that the changeover component 91 locks the first support 25a while the second support 25b is driven by the indexing mechanism successively between its first and last active positions to dispense the unitary doses 2 of its carrier 15.

The invention is not limited to the above disclosed changeover mechanism 90. Any other suitable changeover mechanism 90 that allows for a reliable locking of the unused support 25 and for a releasing at a determined moment, when the first support 25 is in a determined position, to allow the driven support 25 to be changed, could be provided.

Besides, the invention is not limited to a device as above disclosed. For example, the device could comprise more than two supports 25 for more than two carriers. The supports could be of different types and otherwise moveable with respect to the casing. Many aspects of the present invention are applicable to devices with appropriate supports for housing a wide variety of different carriers. In particular, many of the features of the embodiment described below can be used with carriers having a blister pack construction or with carriers having various arrays of housing.

The indexing of the device, in addition to moving the next insert 21 into alignment with the prodgers, actuates the counter mechanism 140 that provides a visual indication to the user of how many unitary doses 2 have been dispensed and/or how may unitary doses 2 remain unused.

An example of a suitable counter mechanism 140, implementing a unit and tens counter driven by a driving gear meshing with one of the gears 78 of the Geneva wheel 76 of the indexing mechanism, is disclosed in WO-A-2005/002654. The driving gear and the unit and tens counters are adapted to index a tens display of the counter display 8 of one number as a unit display of the counter display 8 is indexed from 9 to 0.

What is claimed is:

1. A device for dispensing a plurality of unitary doses of dry powder, comprising:
    a casing provided with a mouthpiece for inhalation by a user;
    first and second supports respectively for two carriers each having a plurality of housings for respective unitary doses adapted to be connected to the mouthpiece for inhalation of the dose, the first and second supports being moveably mounted within the casing for sequentially connecting the housings to the mouthpiece;
    an indexing mechanism adapted to engage and move the first and second supports, the indexing mechanism and the supports being configured so that
    in a first dispensing state of the device, the first support is in engagement with the indexing mechanism so as to be moveable with respect to the casing, and the second support is disengaged from the indexing mechanism so as to be stationary with respect to the casing,
    in a subsequent second dispensing state of the device, the second support is in engagement with the indexing mechanism so as to be moveable with respect to the casing, and the first support is disengaged from the indexing mechanism so as to be stationary with respect to the casing;
    a changeover mechanism adapted to cause the device to pass from the first dispensing state to the second dispensing state and lock the second support in its stationary position while the device is in the first dispensing state, and to lock the first support in its stationary position while the device is in the second dispensing state.

2. The device according to claim 1, wherein the changeover mechanism is further adapted to release the second support from its stationary position and to place the second support into engagement with the indexing mechanism while disengaging the first support from the indexing mechanism.

3. The device according to claim 1, wherein the changeover mechanism is arranged between the first and second supports and is moveably mounted within the casing.

4. The device according to claim 3, wherein the first and second supports comprise first and second engaging portions respectively, the changeover mechanism comprises first and second engaging sections and a locking arrangement arranged to cooperate with the first and second supports so that
    the second engaging section engages the second engaging portion, and the locking arrangement prevents the changeover mechanism from moving with respect to the casing while the device is in the first dispensing state,
    the first and second engaging sections engage respectively the first and second engaging portions, and the locking arrangement allows the changeover mechanism to move with respect to the casing while the first support is disengaging from the indexing mechanism,
    the first engaging section engages the first engaging portion, and the locking arrangement prevents the changeover mechanism from moving with respect to the casing while the device is in the second dispensing state.

5. The device according to claim 4, wherein the first and second supports comprise respectively first and second contact surfaces, and the locking arrangement comprises first and second abutting sections arranged on the changeover mechanism to cooperate respectively with the first and second contact surfaces so that
    the first abutting section abuts the first contact surface while the device is in the first dispensing state,
    the first and second abutting sections do not abut the first and second contact surfaces while the first support is disengaging from the indexing mechanism,
    the second abutting section abuts the second contact surface while the device is in the second dispensing state.

6. The device according to claim 5, wherein the first and second supports further comprise first and second notches arranged respectively in correspondence with the first and second engaging portions, the first and second notches being adapted to remove the abutments of the first and second abutting sections on the first and second contact surfaces while the first support is disengaging from the indexing mechanism.

7. The device according to claim 3, wherein the changeover mechanism is integrally made.

8. The device according to claim 7, wherein the first and second supports are superposed and the changeover mechanism is rotatably mounted within the casing, the changeover mechanism having first and second sides cooperating respectively with the first and second supports.

9. The device according to claim 7, wherein each of the first and second engaging sections is made of gear teeth adapted to mesh with gear teeth of each of the first and second engaging portions, and each of the first and second abutting sections comprises surfaces angularly offset with respect to the respective first and second engaging sections.

10. The device according to claim 9, wherein the respective surfaces of the first and second abutting sections are at least partly formed on the gear teeth of the first and second engaging sections.

11. The device according to claim 1, wherein the first and second supports are of circular configuration, the first and second supports being rotatably mounted within the casing about a central axis.

12. An inhaler comprising a device for dispensing a plurality of unitary doses of dry powder according to claim 1, and two carriers each having a plurality of housings for respective unitary doses, the two carriers being associated respectively with the first and second supports.

13. The device of claim 1, wherein the changeover mechanism comprises:
    an axle;
    a first set of gear teeth extending radially from the axle adapted to engage an engaging portion of the first support while the device is in the second dispensing state; and a second set of gear teeth extending radially from the axle adapted to engage an engaging portion of the second support when the device is in the first dispensing state.

14. The device of claim 13, wherein the axle is located radially outward of the first and second supports and the axle is parallel to an axis of rotation of the first and second supports.

15. The device of claim 1, wherein the changeover mechanism further comprises a first tab extending approximately perpendicular to at least one of the first set of gear teeth; and the first support comprises:
an engagement portion having a plurality of gear teeth around a circumference of the first support;
an outer smooth contact surface covering a portion of the plurality of gear teeth;
a notch in the outer smooth contact surface exposing a plurality of the gear teeth underlying the notch;

wherein in the first dispensing state, the outer smooth contact surface contacts the first tab of the changeover component.

16. The device of claim 15, wherein the plurality of exposed gear teeth engage the first set of gear teeth causing the changeover mechanism to rotate about the axle changing the device from the first dispensing state to the second dispensing state.

17. The device of claim 15 wherein the first support further comprises a decoupling portion having no gear teeth.

18. The device of claim 15, wherein the changeover mechanism comprises a second tab having an abutting surface that contacts a smooth contact surface of the second support in the second dispensing state.

19. The device of claim 18, wherein contact between the abutting surface and the smooth contact surface prevents the changeover mechanism from rotating.

* * * * *